United States Patent [19] [11] 4,298,691
Veeder et al. [45] Nov. 3, 1981

[54] PREPARATION OF HETEROPOLYSACCHARIDE S-156

[75] Inventors: George T. Veeder, San Diego; Kenneth S. Kang, LaJolla, both of Calif.

[73] Assignee: Merck & Co., Inc., Rahway, N.J.

[21] Appl. No.: 184,597

[22] Filed: Sep. 5, 1980

[51] Int. Cl.³ .......................................... C12P 19/04
[52] U.S. Cl. .................................. 435/101; 435/104; 435/852; 260/17.4 ST; 536/1; 536/114
[58] Field of Search ...................... 435/101, 104, 852; 260/17.4 ST; 536/1, 114

[56] References Cited

U.S. PATENT DOCUMENTS

| | | | |
|---|---|---|---|
| 4,186,025 | 1/1980 | Kang et al. | 435/852 X |
| 4,218,538 | 8/1980 | Church | 435/101 |
| 4,247,639 | 1/1981 | Kang et al. | 435/101 |
| 4,259,451 | 3/1981 | Steenbergen et al. | 435/253 |

Primary Examiner—Lionel M. Shapiro
Attorney, Agent, or Firm—Gabriel Lopez; Hesna J. Pfeiffer

[57] ABSTRACT

A process for producing heteropolysaccharide S-156 by bacterial fermentation of an organism deposited with the American Type Culture Collection under Accession No. ATCC 31646.

7 Claims, No Drawings

PREPARATION OF HETEROPOLYSACCHARIDE S-156

CROSS REFERENCE

This application is related to another application filed Sept. 5, 1980, Ser. No. 184,500 entitled "Use of Heteropolysaccharide S-156 in Latex Paint."

BACKGROUND OF THE INVENTION

It is known that heteropolysaccharides can be produced by certain microorganisms. Some of such heteropolysaccharides function as hydrophilic colloids and because of their viscosity properties and rheology have been used as thickening agents for aqueous systems.

A polysaccharide of composition similar to S-156 has been described as *Klebsiella pneumoniae* K-type 63 (Carb. Res. (1979) 77, pp 183-190). Another is *E. coli* serotype K-42 (op. cit.).

SUMMARY OF THE INVENTION

It has now been found that a variant strain of *K. pneumoniae*, ATCC 31646, produces a water-soluble heteropolysaccharide of composition similar to that described for *K. pneumoniae* K-63 when incubated in a selected nutrient medium. An unrestricted deposit of this hitherto undescribed organism was made with the American Type Culture Collection on May 12, 1980, under Accession No. ATCC 31646. It is listed with the ATCC as a Class 2 agent.

When this organism is grown in a low nitrate medium, it produces a polysaccharide of high viscosity.

DETAILED DESCRIPTION

This organism was isolated from a soil sample obtained from Nassau, N.Y. The organism was picked as a gummy colony after 4 days' incubation at 30° C. from an E-1 agar plate containing 1% glucose as the carbon source and 100 ppm of methyl green. The isolate was then pure cultured on nutrient agar.

A YM seed flask was started with a fresh NA plate and placed on a gyrotary shaker at 30° C. Approximately 24 hrs later this seed was used to inoculate two E-1 flasks, one containing 3% glucose and one containing 3% hydrolyzed starch as carbon sources. These flasks were placed on a shaker at 30° C. Approximately 72 hrs later, the following results were obtained.

| Flask | pH | Beer Vis. (cP) | Gum Yield (gm) |
|---|---|---|---|
| Starch | 6.6 | 1400 | 0.81 |
| Glucose | ND | none | none |

Another YM seed flask was prepared in the above fashion and used at 24 hrs to inoculate 7 different media containing 3% hydrolyzed starch as the carbon source. These flasks were incubated on a shaker at 30° C. for about 72 hrs at which time the pH, viscosity, gum yield, and product viscosity were measured. The results are shown below:

| Medium | | pH | Vis. (cP)* | Gum Yield | % Product Vis. (cP)* |
|---|---|---|---|---|---|
| E-1 | | 5.5 | 9,750 | 1.26 | ND** |
| E-1 | + TE** | 6.1 | 31,600 | 1.52 | 4050 |
| E-1 | − NH$_4$NO$_3$ + 0.191% NaNO$_3$ | 6.5 | 26,500 | 1.52 | ND |
| E-1 | − Promosoy | 5.6 | 7,400 | 1.30 | ND |
| E-1 | − Promosoy + 0.025% fish solubles | 6.1 | 13,300 | 1.30 | ND |
| E-1 | + 0.1% Promosoy | 5.9 | 13,825 | 1.45 | ND |
| E-1 | + 0.1% YE** | 6.3 | 8,500 | 1.44 | ND |

*Brookfield LVF viscometer, 60 rpm, spindle 4, room temp. for visc. <10,000 cP, 30 rpm for visc. 10,000-20,000 cP, and 12 rpm for visc. >20,000 cP.
**ND = not determined
TE = 0 Trace elements
YE = Yeast extract E-1 medium contains 5 gms of dipotassium phosphate, 0.1 gm of magnesium sulfate, 0.9 gm of ammonium nitrate, 0.5 gm of Promosoy 100 (an enzymatic digest of soybean meal sold by Central Soya, Chemurgy Division), 30 gms of dextrose and 1 liter of tap water. The pH of the E-1 medium is about 7.6 to 7.8.

Subsequent scale-ups have demonstrated that the ammonium nitrate concentration has an effect on product quality. Specifically, the E-1 medium (high NH$_4$NO$_3$) produces a lower viscosity gum than the following basal medium (low NH$_4$NO$_3$). Quantities are shown as % (wt/vol):

| Basal-1 Medium | |
|---|---|
| 0.05% | K$_2$HPO$_4$* |
| 0.01% | MgSO$_4$ . 7H$_2$O |
| 0.06% | NH$_4$NO$_3$ |
| 0.05% | Promosoy |
| 1 ppm | Fe++ |

Another preferred medium is:

| Basal-2 Medium | |
|---|---|
| 0.05% | Na$_2$HPO$_4$* |
| 0.01% | MgSO$_4$ . 7H$_2$O |
| 0.045% | NH$_4$NO$_3$ |
| 0.05% | Promosoy |

ATCC 31646 has been identified as a *K. pneumoniae* strain using the API system.

FERMENTATION CONDITIONS

Heteropolysaccharide S-156 is produced during the aerobic fermentation of suitable aqueous nutrient media under controlled conditions via the inoculation with the organism ATCC 31646. The media are usual media containing sources of carbon, nitrogen and inorganic salts.

In general, carbohydrates (for example, glucose, fructose, maltose, sucrose, xylose, mannitol, starch, corn syrup, and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 5% by weight of the medium. These carbon sources can be used individually or several such carbon sources may be combined in the medium. In general, many proteinaceous materials may be used as nitrogen sources in the fermentation process. Suitable nitrogen sources include, for example, yeast hydrosylates, primary yeast, soybean meal, cottonseed flour, hydrolysates of casein, cornsteep liquor, distiller's solubles or tomato paste and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as iron and magnesium.

It should be noted that the media described in the examples are merely illustrative of the wide variety of media which may be employed, and are not intended to be limiting.

As an alternate medium, S-156 may be grown under low $Ca^{++}$ conditions, i.e., in deionized water or some other aqueous system substantially free of $Ca^{++}$ ions, (i.e., less than about 4 ppm $Ca^{++}$ per 1% gum in the final fermentor broth.)

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 31646 culture and producing the polysaccharide S-156 can vary from about 6.0 to 7.5.

Although the polysaccharide S-156 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol, conveniently in the form of CBM (an 85:15 alcohol:water constant boiling mixture).

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-156 is particularly suited for the preparation of large quantities.

Although ATCC 31646 can be grown under a broad spectrum of media conditions, the following preferred conditions are recommended.

1. Culture Maintenance

The culture grows quite well on nutrient agar (NA) or YM agar, but NA is preferred for culture maintenance.

2. Seed Preparation

Seed preparation for this organism is started in YM broth incubated at 30° C. The YM seeds are then used at 24-30 hrs. to inoculate seed medium. The composition of the seed medium is as follows:

3.0% Hydrolyzed starch (DE 16-26)*
0.5% $K_2HPO_4$
0.05% Promosoy 100
0.06% $NH_4NO_3$
0.01% $MgSO_4.7H_2O$
1 ppm $Fe^{++}$

*The starch may be hydrolyzed with commercially available α-amylases.

A 5 to 10% inoculum size is used at 24-30 hrs. to inoculate the final fermentor.

3. 70L Fermentor Medium 3.0% Hydrolyzed Starch*
0.05% $K_2HPO_4$
0.05% Promosoy 100
0.06% $NH_4NO_3$
0.01% $MgSO_4.7H_2O$
1 ppm $Fe^{++}$

*Low DE starch (DE 16-26) is preferred for a high viscosity product.

The pH should be controlled at 6.5-7.0; the temperature at 30° C.

Fermentation times range from about 70-90 hrs. with beer viscosity exceeding 100,000 cP. Conversion efficiencies vary from 54-69 with 3% starch. Antifoam SAG 471 (Union Carbide) is used.

4. Recovery

On completion of the fermentation, (residual carbon source less than 0.3%), the heteropolysaccharide S-156 may be recovered by treatment of the fermentation beer with a miscible solvent which is a poor solvent for the heteropolysaccharide and does not react with it. In this way the heteropolysaccharide is precipitated from solution. The quantity of solvent employed generally ranges from about 2 to about 3 volumes per volume of fermentation beer. Among the various solvents which may be employed are acetone and lower alkanols such as methanol, ethanol, isopropanol, n-butanol, sec-butanol, tertiary butanol, iso-butanol, and n-amyl alcohol. Isopropanol is preferred. Precipitation of S-156 is facilitated when the fermentation beer is first heated to a temperature of about 70° C. to 75° C. for a short time, e.g., about 5 to 10 minutes, and then cooled to about 30° C. or lower before addition of the solvent. This heat treatment also destroys cellulase enzymes produced during the fermentation. Thus, this is a preferred method of precipitating the heteropolysaccharide from the fermentation beer. The solid is recovered by separating it from the liquid, as by filtering or straining and then drying at elevated temperature.

5. Drying

The product is dried at 55° C. for up to one hour in a forced-air tray drier.

6. Product Quality

One percent deionized water viscosities range from about 3200 to about 3850 cP as a measured on a Brookfield LVF, spindle 4, 60 rpm at room temperature.

COMPOSITION OF HETEROPOLYSACCHARIDE S-156

The heteropolysaccharide produced by ATCC 31646 is composed of principally carbohydrate, 5.5 to 7% acetyl groups as the O-glycosidically linked ester, no pyruvate, and 6-8% protein.

The carbohydrate portion of the S-156 polysaccharide contains galacturonic acid (20-23% b.o. wt. gum) and the neutral sugars galactose and fucose. The approximate molar rato of galactose to fucose is 45:55. As the heteropolysaccharide contains about 70% carbohydrate, the approximate molar ratio galacturonic acid:-galactose:fucose is about 23:21:26.

The acetyl content was determined by treating a 0.2% aqueous solution of S-156 gum with an alkaline, hydroxylamine reagent followed by treatment with an acidic ferric chloride reagent [S. Hestrin (1949) J. Biol. Chem. 180 249-261].

The neutral sugars of polysaccharide S-156 were determined by dissolving ten mg. of the product in 2 ml 2 N $H_2SO_4$, and the mixture is heated at 100° C. for 4 hours. The resulting solution is cooled, neutralized with barium hydroxide and the pH is brought to 5-6 with solid carbon dioxide. The resulting precipitate of barium sulfate is removed by centrifugation and the supernatant is concentrated to a syrup under reduced pressure. The sugars in the hydrolysate are tentatively identified by gas-liquid chromatography of their aldononitrile acetate derivatives on a Hewlett-Packard Model 5830A chromatograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) Carbohydr. Res. 27 464-467].

The various neutral sugars of the polysaccharides were also characterized by use of descending paper chromatography on Whatman No. 1 chromatography paper using as the solvent the upper layer of pyridine-:ethyl acetate:water (2:5:5). Chromatograms were stained using silver nitrate dip and acid aniline phthalate spray reagent. Component sugars were identified by co-chromatography with sugar standards and by the specific color reaction with the analine phthalate reagent.

The uronic acid content of the polysaccharide was determined by decarboxylation with 19% hydrochloric acid; the liberated carbon dioxide was trapped in standard sodium hydroxide and determined by back titration [B. L. Browning (1967) *Methods of Wood Chemistry* II, 632-633].

Paper electrophoresis was used for the separation and tentative identification of the uronic acids present in the neutralized acid hydrolysate described above. Aliquots of this and known uronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. One uronic acid spot was found by this method.

S-156 is compatible with both methylene blue chloride and xylene milling green B. The viscosity of the gum is only slightly sensitive to salt and brine and shows a good stability to changes in pH over a range of 1.0 to 11.5. The viscosity is also stable in the presence of high $CaCl_2$ concentrations. It is not soluble in ammonium polyphosphate at a 0.25% concentration. Synergism is observed with CMC, Guar, HEC, locust bean gum and Poly-ox. This gum shows good alkaline stability, but has very poor acid stability. When heated to 149° C., a 99% viscosity reduction is observed, but on cooling to 27° C., 10% of the viscosity is regained. S-156 is cellulase negative, however, there is evidence of slight gumase activity.

A beige sample of S-156 which is a 40 mesh powder having a moisture content of 9.6% exhibits the following properties:

| 1. Viscosity vs. Concentration (room temp.) Brookfield Visc. (cP) | | | |
|---|---|---|---|
| Conc. | D.I. Water | 0.1% KCl | Brine |
| 0.05% | 21 | 7.5 | 4.2 |
| 0.10% | 39 | 15 | 6.5 |
| 0.50% | 360 | 340 | 240 |
| 1.00% | 2200 | 2350 | 2125 |

| 2. Visc. vs. pH, 1% in D.I. Water (room temp.) | |
|---|---|
| pH | Brookfield Visc. (cP) |
| 1.0 | 1750 |
| 2.0 | 2000 |
| 3.0 | 2125 |
| 4.0 | 2050 |
| 6.0 | 2025 |
| 7.0 | 2100 |
| 7.8 | 2075 |
| 8.8 | 2150 |
| 9.8 | 2225 |
| 10.8 | 2200 |
| 11.5 | 2050 |

| 3. Shirley-Ferranti Rheology (room temp.) | | |
|---|---|---|
| A 1% gum solution in deionized water with 0.1% potassium chloride is used for this test. | | |
| Shear Rate (sec$^{-1}$) | Shear Stress (dynes/cm$^2$) | Visc. (cP) |
| 0.2 × 10$^3$ | 960 | 440 |
| 1.0 × 10$^3$ | 1200 | 130 |
| 2.0 × 10$^3$ | 1420 | 71 |
| 4.0 × 10$^3$ | 1780 | 45 |
| 6.0 × 10$^3$ | 2040 | 34 |
| 8.0 × 10$^3$ | 2240 | 28 |
| 10.0 × 10$^3$ | 2460 | 24 |
| 12.0 × 10$^3$ | 2660 | 22 |
| 14.0 × 10 | 2880 | 21 |
| 15.6 × 10$^3$ | 3000 | 19 |

In a preferred embodiment of the invention, S-156 is dialdehyde-treated to produce a more readily dispersible powder. The preferred dialdehyde is glyoxal.

S-156 has improved dispersibility in aqueous systems if S-156 beer is heated in the presence of a dialdehyde at an acid pH. The process comprises heating the aqueous medium containing the dissolved biogum and having a pH of 7 or below, preferably a pH of 4.5 to 7, to a temperature of from 70° C. to 100° C. for a time sufficient to improve dispersibility of the recovered biogum, the heating taking place in the presence of from 0.5% to 15% by weight of a dialdehyde based on the dry weight of the biogum in the aqueous medium, and recovering the dissolved biogum from the medium. The dialdehyde is present during this heat treatment in an amount of at least about 0.5% based on the weight of the dry S-156 gum in the beer. While amounts of dialdehyde up to 15% by weight of the dry gum in the beer may be used, in general amounts greater than 3% do not usually confer any discernible improvement.

The aldehyde may be an aliphatic dialdehyde of from 2 to 8 carbon atoms, e.g. glyoxal, malonaldehyde, succinaldehyde, glutaraldehyde, adipinaldehyde or octandialdehyde, or polyglyoxal, an oligomeric form of glyoxalhydrates having from 5 to 10 glyoxalhydrate repeating units. Glyoxal is preferred.

The dialdehyde is added to the beer at about the completion of the fermentation process, preferably with agitation to obtain uniform distribution of the dialdehyde. The beer is then heated to a temperature of from 70° C. to 100° C. for a time sufficient to improve the dispersibility of the recovered biogum. In general, this takes at least about 2 minutes, typically from about 2 to about 5 minutes. While the heating times may be longer, no additional improvement is seen in dispersibility after about 5 minutes of heating.

Heating in the presence of a dialdehyde at a pH below about 7 to obtain improved dispersibility is most conveniently and economically carried out by combining the dialdehyde treatment with pasteurization by heating. In this way no additional time or heating expense is required for the dialdehyde treatment beyond the cost of the dialdehyde itself. While the foregoing has described the process with reference to a fermentation beer, the process is not limited to fermentation beers but is applicable to any aqueous solution of S-156.

It has been found that Heteropolysaccharide S-156 may be used by incorporating it into a conventional water base paint formulation to thicken the paint and to give it many desirable properties. Suitable quantities of Heteropolysaccharide S-156 are from about 0.1 to about 1% by weight of the paint; a preferred range is from about 0.3 to 0.5% by weight of the paint. Within this effective range, S-156 advantageously does not interfere with the inherent gloss of the coating and is readily dispersed and solublized in cold or hot water.

In forming water base paints which contain an effective quantity, e.g., about 0.1 to about 1% by weight of the paint, of the heteropolysaccharide of the invention to thicken said paint, the paint contains an aqueous latex emulsion composition containing a resinous film-forming agent and a pigment. The paint may also contain other ingredients such as extenders, anti-foaming agents, dispersion agents, freeze-thaw stabilizers and preservatives.

The coating compositions of the present invention may also contain one or more film forming binders. As used herein, the term "film-forming binder" is intended to embrace those water soluble or water dispersible film-forming resins conventionally employed in latex paint compositions. These include aqueous colloidal dispersions of polymers from the polymerization of monomers such as acrylic acid, methacrylic acid, methylmethacrylate, ethylmethacrylate, ethylhexylacrylate, tetrafluoroethylene, chlorotrifluoroethylene, vinylidene fluoride, butadiene-1,3, isoprene, chloroprene, styrene, nitriles, acrylamides, vinyl alcohol, methacrylamide, acrylonitrile, vinyl chloride, vinyl acetate, vinylidene chloride, ethylene, propylene and isobutylene; drying oil fatty acid compounds such as tung oil, linseed oil, soybean oil, dehydrated castor oil, cottonseed oil, poppyseed oil, safflower oil, and sunflower oil; fatty acids derived from drying oils; partially polymerized drying oils such as partially polymerized linseed oil; oxidized drying oils such as oxidized soybean oil, synthetic drying oils obtained by the esterification of fatty acids with polyhydric alcohols (e.g., glycerol pentaerythritol, mannitol and sorbitol); drying oil—alkyd resins of the type obtained by reacting a drying oil fatty acid with polyhydric alcohol and a polycarboxylic acid such as maleic anhydride, fumaric acid, phthalic acid, adipic acid, sebacic acid, and the like; latices of chlorinated and natural rubbers, the polysulfides, epoxides, amino resins such as urea-formaldehyde, malamineformaldehyde, Nitcocellulose, ethyl cellulose, cellulose butyrate, chlorinated poly ethers, terpene resins, chlorosulfonated polyethylene natural rubber, organo siloxane polymers, as well as other film-forming binders employed in water based paints.

Suitable commercially available polymeric latex formulations generally contain from about 40 to 60 weight percent of an emulsified polymer and include by way of non-limiting example, natural rubber, styrene-butadiene copolymer, butadiene-acrylonitrile copolymers, polyvinyl chloride, polyvinyl acetate, copolymers of vinylidene chloride and acrylonitrile, polytetrafluoroethylene, ethylacrylate-methacrylate copolymers, butadiene-styrene-acrylonitrile copolymers, isobutylene-isoprene copolymers, acrylonitrilebutylacrylate-methacrylic acid copolymers, styrene-butyl acrylateacrylic acid copolymers, copolymers of styrene, acrylonitrile, octyl acrylate and methacrylic acid, copolymers of methyl methacrylate, ethyl acrylate and ammonium methacrylate.

Pigments contemplated in the present compositions include colored as well as white pigments and is understood to be inclusive of mineral products used as fillers and extenders. Suitable pigments include the various water insoluble organic and inorganic paint pigments such as titanium dioxide, zinc oxide, phthalocyanine blue and green, lead chromate, molybdate orange, zinc sulfide, calcium sulfate, barium sulfate (barytes), clay, mica, calcium carbonate (whiting), silica, benzylidene yellow, cadmium yellow, toluidine toners, sienna, amber, ultramarine blues, chromium oxides, carbon black, antimony oxide, magnesium silicate (talc), aluminum silicate, lead silicate, graphite, aluminum oxide, calcium silicate, diatamaceous silica, limonite, hematite, magnetite, siderite, selenium sulfides, calcined nickel titanate dioxide, molybdate oranges, chrome green, iron blues, benzidene yellows and oranges, iron salts of nitroso compounds, Hanso yellows, Di-nitraniline oranges, permanent red 2B types and the like in various combinations and preparations depending on the end use for which the paint is designed.

Water base paints may also include quite a variety of wetting or dispersing agents such as polyphosphates, pyrophosphates, anionic and non-ionic surfactants, polyacrylates, polymethacrylates, polyvinyl alcohol, and polyethylene-glycol. Additional ingredients include freeze-thaw stabilizers such as ethylene glycol, diethylene glycol, and non-ionic surfactants; and preservatives such as organo-mercuric and organo-tin compounds, alkylated, halogenated or arylated phenols and their derivatives, antibiotics and many others. Still other ingredients may be included in water base paint formulae which are materials known as foam breakers, e.g. silicones, ditertiary acetylenic glycols, long chain ethylene oxide condensates, tributyl phosphate, pine oil and higher aliphatic alcohols. Water base paints including Heteropolysaccharide S-156 may also include such materials as starch, casein, methyl cellulose, hydroxy ethyl cellulose, vegetable gum, and synethetic thickeners.

The addition of Heteropolysaccharide S-156 to the pigment grind assists in the dispersing of the pigment. The dispersing characteristics of Heteropolysaccharide S-156 permit formulation of paints according to this invention while using substantially less surfactant than is required generally in paints to disperse the pigment. Through reduction of the surfactant content, paints can be produced which have improved water resistance.

It is advantageous to add at least a portion of S-156 to the pigment grind. The various pigments employed in the paint are generally ground in a mixer, such as a Cowless Dissolver, prior to addition of the paint binder which is mixed to form the finished paint. The presence of Heteropolysaccharide S-156 in the pigment grind assists in the dispersing of the pigment. The concentrate of heteropolysaccharide in the pigment grind may range from 1 to 4 lbs. per 100 gallons of the finished paint but preferably ranges from 1 to 2 lbs. per 100 gallons of the finished paint.

Any additional Heteropolysaccharide S-156 used in the paint (in addition to that added to the pigment grind) is generally in the form of an aqueous presolution. The aqueous presolution is generally added during the letdown of the paint.

The invention is further defined by reference to the following examples, which are intended to be illustrative and not limiting.

EXAMPLE 1

Preparation Of S-156

Seed preparation is started in YM broth incubated at 30° C. The YM seeds are used at 24 hours to inoculate 3000 ml. of seed medium which is composed of:

| | |
|---|---|
| 3% | Starch (DE 16–26) |
| 0.05% | K$_2$HPO$_4$ |
| 0.01% | MgSO$_4$ . 7H$_2$O |
| 0.06% | NH$_4$NO$_3$ |
| 0.05% | Promosoy 100 |
| 1 ppm | Fe$^{+++}$ |
| 0.1% | SAG 471 Antifoam |

At 24 hours, 3000 ml of this medium is used to inoculate 20 L and 70 L fermentors containing:

| | |
|---|---|
| 3% | Starch (DE 16–26) |
| 0.05% | K$_2$HPO$_4$ |
| 0.01% | MgSO$_4$ . 7H$_2$O |
| 0.06% | NH$_4$NO$_3$ |
| 0.05% | Promosoy 100 |
| 1 ppm | Fe$^{++}$ |
| 0.04% | SAG 471 Antifoam |

The following data are obtained:

| Fermentor | Age (hrs) | Beer* Visc. (cP) | RCS (%) | Yield (%) | 1% Product* Visc. (cP) |
|---|---|---|---|---|---|
| 2OL #1 | 23.5 | 3,150 | 0.92 | 1.72 | — |
|  | 44.0 | >100,000 | ND | ND | — |
|  | 70.0 | >100,000 | 0.26 | 1.91 | 3200 |
| 2OL #2 | 23.5 | 3,300 | 1.10 | 1.77 | — |
|  | 44.0 | >100,000 | ND | ND | — |
|  | 70.0 | >100,000 | 0.24 | 1.91 | 3325 |
| 7OL #1 | 22.5 | 430 | ND | ND | — |
|  | 46.5 | 17,000 | 0.41 | 1.75 | — |
|  | 70.0 | >100,000 | ND | 1.76 | — |
| 7OL #2 | 66.0 | 18,500 | 0.10 | 1.83 | — |
|  | 86.0 | >100,000 | 0.10 | 1.86 | 3850 |

*Brookfield LVF, 60 rpm, spin. #3, R.T. for visc. <2000 cP; spin. #4, 60 rpm for 2000–10,000 cP; spin. #4, 6 rpm for >10,000 cP.

At the completion of fermentation (RCS less than 0.3%), the polysaccharide is recovered by precipitation with the 2–3 volumes of isopropanol and the fibers collected and dried at 55° C. for up to one hour.

When E-1 medium and 3% starch as the carbon source is used instead of Basal-1 medium, the product is of low viscosity:

| Fermentor | Age (hrs) | Beer* Visc (cP) | RCS (%) | Yield (%) | 1% Product* Visc. (cP) |
|---|---|---|---|---|---|
| 2OL # | 39.0 | 4,700 | 0.33 | 1.51 | — |
|  | 62.5 | 7,350 | 0.25 | 1.62 | — |
|  | 89.5 | 7,800 | 0.18 | 1.73 | 1160 |
| 2OL #2 | 39.0 | 2,450 | 0.45 | 1.33 | — |
|  | 62.5 | 7,500 | 0.33 | 1.57 | — |
|  | 89.5 | 7,500 | 0.22 | 1.62 | 1320 |
| 2OL #3 | 39.0 | 5,500 | 0.40 | 1.51 | — |
|  | 62.5 | 8,750 | 0.36 | 1.72 | — |
|  | 89.5 | 39,500 | 0.26 | 1.80 | 1560 |

*Brookfield LVF, 60 rpm, spin. #4, R.T. for 10,000 cP; spin. #4, 6 rpm for >10,000 cP

EXAMPLE 2

Glyoxal Treatment of Heteropolysaccharide S-156

45 L of beer in a 70 L fermentor are treated with 9 N H$_2$SO$_4$ to adjust the pH to 5.5. Glyoxal (37.5 ml, 40% w/w) is then added and the temperature raised to 77° C. After holding this temperature for five minutes, the beer is cooled and the gum recovered by precipitation with IPA followed by drying and milling.

This process produces tan colored, medium sized granules of S-156 with a moisture content of approx. 13% and an ash content (dry basis) of approx. 17%. This polysaccharide has the following profile of properties (all measurements at room temperature):

| Conc. (%) | Viscosity* vs. Concentration | | | |
|---|---|---|---|---|
|  |  | Visc. (cP) | | |
|  | Spin. | RPM | STW** | D.I.H$_2$O |
| 1.00 | 4 | 60 | 2400 | 2400 |
| 0.50 | 2 | 60 | 305 | |
| 0.10 | 1 | 60 | 13 | |
| 0.10 | U.L. adap. | 60 | 8.09 | |
|  | U.L. adap. | 6 | 13.5 | |
| 0.05 | U.L. adap. | 60 | 4.02 | |
|  | U.L. adap. | 6 | 5.0 | |
| 0.01 | U.L. adap. | 60 | 1.5 | |
|  | U.L. adap. | 6 | 2.5 | |

*Brookfield LVT viscometer
**Synthetic Tap Water (1000 ppm NaCl, 100 ppm CaCl$_2$, in D.I. water).

EXAMPLE 3

Evaluation of Native S-156 in AC-417 Semi-Gloss Latex Paint

A latex coating is formulated from the following ingredients:

| Material | Pounds |
|---|---|
| 1. Water | 73.0 |

| | Material | Pounds |
|---|---|---|
| 2. | Preservative (Dowicil® 75, Dow Chemical Co., Midland, Michigan) | 2.0 |
| 3. | Dispersant (Tamol® 731, Rohm and Haas Co., Philadelphia, Pennsylvania | 9.0 |
| 4. | Propylene glycol | 60.0 |
| 5. | Ethylene glycol | 15.0 |
| 6. | Carbitol® solvent (Union Carbide, Corp., New York, New York) | 18.0 |
| 7. | Defoamer (Colloid® 600, Colloids, Inc., Newark, New Jersey) | 2.0 |
| 8. | Surfactant (Aerosol® OT, American Cyanamid Corp., Wayne, New Jersey) | 2.0 |
| 9. | Pigment (TiPure® R-900, DuPont, Wilmington, Delaware) | 270.0 |
| 10. | Heteropolysaccharide S-156 | 3.0 |
| 11. | Water | 124.0 |
| 12. | Latex (Rhoplex® AC-417, Rohm and Haas, Philadelphia, Pennsylvania) | 433.0 |
| 13. | Defoamer (Nopco NDW, Diamond Shamrock Corp., Morristown, New Jersey) | 3.0 |
| 14. | Water | 65.0 |
| | TOTAL | 1079.0 |

Materials 1–10 are charged to a high speed dispenser in order of listing with low speed agitation. After the ingredients are added, grinding at high speed is carried out for about 30 minutes or until a 7 Hegman grind is obtained, while maintaining the temperature below 54° C. (130° F.). The remaining ingredients are then added in order of listing and mixed at low speed until the composition is uniform. The paint had the following properties. Viscosities are shown in Krebs Units (KU).

| Viscosity | |
|---|---|
| Initial | 77 KU |
| 120° F. (49° C.) heat stability (four weeks) | 75 KU |
| Ambient temp. stability (four weeks) | 77 KU |
| 60 degree Gloss units | 71 |

For comparative purposes, a paint composition was prepared following the procedure of Example 3, except that hydroxyethyl cellulose (NATROSOL® 250 HR, Hercules, Inc., Wilmington, Del.) is substituted for Heteropolysaccharide S-156. The following results were obtained:

| Viscosity | |
|---|---|
| Initial | 77 KU |
| 120° F. (49° C.) heat stability (four weeks) | 88 KU |
| Ambient temp. stability (four weeks) | 81 KU |
| 60 degree Gloss units | 56 |

In addition to the improved heat stability and gloss retention over the paint composition containing hydroxyethyl cellulose, the S-156 paint composition has superior flow properties and improved brushing characteristics.

EXAMPLE 4

Evaluation of Glyoxal-Treated S-156 in AC-417 Semi-Gloss Latex Paint

A paint composition is prepared following te procedure of Example 3, except that glyoxal-treated Heteropolysaccharide S-156 is substituted for native Heteropolysaccharide S-156. The following results are obtained:

| Viscosity | |
|---|---|
| Initial | 77 KU |
| Ambient temperature stability (four weeks) | 77 KU |
| 120° F. (49° C.) heat stability (four weeks) | 75 KU |
| 60 degree Gloss units | 70 |

In addition to heat stability and 60 degree gloss, the glyoxal-treated S-156 has flow properties and brushing characteristics similar to those of native S-156.

EXAMPLE 5

Evaluation of Glyoxal-Treated S-156 in RHOPLEX® AC-388 Semi-Gloss Paint

| | Material | Pounds |
|---|---|---|
| 1. | Water | 73 |
| 2. | Preservative (Dowicil® 75, Dow Chemical Co., Midland, Michigan) | 2.0 |
| 3. | Dispersant (Tamol® 731, Rohm and Haas Co., Philadelphia, Pennsylvania) | 9.0 |
| 4. | Propylene glycol | 60.0 |
| 5. | Ethylene glycol | 15.0 |
| 6. | Carbitol® Solvent Union Carbide Corp, New York, New York) | 18.0 |
| 7. | Defoamer (Colloid® 600, Colloids, Inc., Newark, New Jersey) | 2.0 |
| 8. | Surfactant (Aerosol® OT, American Cyanamid Co., Wayne, New Jersey) | 2.0 |
| 9. | Pigment (TiPure® R-900 | 250 |
| 10. | Heteropolysaccharide S-156 (glyoxal-treated) | 3.0 |
| 11. | Water | 154 |
| 12. | Latex (Rhoplex® AC-388) Rohm and Haas, Philadelphia, Pennsylvania | 458 |
| 13. | Defoamer (Nopco NDW, Diamond Shamrock Corp., Morristown, New Jersey) | 2 |
| | TOTAL | 1048 |

Material 1–10 are charged to a high speed disperser in order of listing with low speed agitation. After the ingredients are added, grinding at high speed is carried out for about 30 minutes, or until a 7 Hegman grind is obtained, while maintaining the temperature below 54° C. (130° F.) The remaining ingredients are then added in order of listing and mixed at low speed until the composition is smooth. The paint has the following properties:

| KU viscosity (Kreb Units) | |
|---|---|
| Initial | 86 |
| 15 minutes in Waring Blender at high speed | 86 |

| KU viscosity (Kreb Units) | |
| --- | --- |
| 60 degree Gloss units | 60 |

For comparative purposes, a paint composition was prepared following the procedure of Example 5, except that hydroxyethyl cellulose (NATROSOL ® 250 MR, Hercules, Inc., Wilmington, Del.) is substituted for glyoxal-treated Heteroolysaccharide S-156. The following results were obtained:

| KU viscosity (Kreb Units) | |
| --- | --- |
| Initial | 86 |
| 15 minutes in Waring Blender at high speed | 83 |
| 60 degree Gloss units | 50 |

In addition to high shear stability and improved gloss retention over the paint composition containing hydroxyethyl cellulose, the heteropolysaccharide paint composition has superior flow and leveling properties and improved brushing characteristics.

EXAMPLE 6

Evaluation of Glyoxal-Treated S-156 in UCAR ® 366 Flat Latex Paint

| | Material | Pounds |
| --- | --- | --- |
| 1. | Water | 100 |
| 2. | Preservative (Dowicil ® 75, Dow Chemical Co., Midland, Michigan) | 2 |
| 3. | Dispersant (Tamol ® 731, Rohm and Haas, Co., Philadelphia, Pennsylvania) | 11 |
| 4. | Buffer (AMP-95, IMC Chemical Group, Inc., Des Plaines, Illinoia) | 4 |
| 5. | Surfactant (Aerosol ® OT, American Cyanamid Co., Wayne, New Jersey) | 2 |
| 6. | Defoamer (Nalco 2300, Nalco Chemical Co., Oak Brook, Illinois) | 2 |
| 7. | Ethylene glycol | 20 |
| 8. | TEXANOL ® Solvent (Eastman Chemical Products, Inc., Kingsport, Tennessee) | 8 |
| 9. | Pigment (TiPure ® R-900, DuPont, Wilmington, Delaware | 100 |
| 10. | Silica (Celite ® 281, Johns-Manville Corp., Denver, Colorado) | 50 |
| 11. | Calcium carbonate (Atomite ®, Thompson, Weinman, Inc., Cartersville, Georgia) | 125 |
| 12. | Aluminum silicate (Minex 4, Indusmin Ltd., Toronto, Ontario, Canada | 100 |
| 13. | Aluminum silicate (Huber 80C, J.M. Huber Corp., Edison, New Jersey) | 100 |
| 14. | Heteropolysaccharide S-156 (glyoxal-treated) | 2 |
| 15. | Water | 88 |
| 16. | Latex (UCAR ® 366, Union Carbide Corp. New York, New York) | 192 |
| 17. | Surfactant (Triton ® GR7M, Rohm and Haas Co., Philadelphia, Pennsylvania) | 2 |
| 18. | Defoamer (Nalco 2303, Nalco Chemical Co., Oak Brook, Illinois) | 4 |
| 19. | Heteropolysaccharide S-156 (2% dissolved in water) | 150 |
| | TOTAL | 1162 |

Materials 1-14 are charged to a high speed dispenser in order of listing with low speed agitation. After the ingredients are added, grinding at high speed is carried out for about 30 minutes, or until a 4 Hegman grind is obtained, while maintaining the temperature below 54° C. (130° F.) The remaining ingredients are then aded in order of listing and mixed at low speed until the composition is smooth. The resulting coating has excellent flow and leveling properties, good sag resistance, good package stability, good color acceptance, reduction of syneresis, and good resistance to latex and pigment shock.

What is claimed is:

1. A process for producing heteropolysaccharide S-156 which comprises growing the organism ATCC 31646 in an aqueous nutrient medium by aerobic fermentation of an assimilable carbohydrate source and recovering said heteropolysaccharide S-156.

2. A process of claim 1 wherein the carbohydrate source is 3% (w/v) hydrolyzed starch.

3. A process of claim 2 wherein the starch is of DE 16-20.

4. A process of claim 2 wherein the nutrient medium contains no more than about 0.06% (w/v) $NH_4NO_3$.

5. A process of claim 1 wherein the nutrient medium comprises 3% hydrolyzed starch (DE 16-26), 0.05% $K_2HPO_4$, 0.05% enzymatic digest of soybean meal, 0.06% $NH_4NO_3$, 0.01% $MgSO_4.7H_2O$, and 1 ppm $Fe^{++}$.

6. A process of claim 1 wherein the nutrient medium is substantially free of $Ca^{++}$.

7. A process for producing dialdehyde-treated Heteropolysaccharide S-156 which comprises growing the organism ATCC 31646 in an aqueous nutrient medium by aerobic fermentation of an assimilable carbohydrate source and on completion of said fermentation heating the aqueous nutrient medium at a pH of 4.5 to 7 to a temperature of 70° C. to 100° for about 2 to 5 minutes in the presence of from 0.5% to 15% by weight of dialdehyde said weight based on the dry weight of Heteropolysaccharide S-156 in said medium and then recovering said dialdehyde-treated Heteropolysaccharide S-156.

* * * * *